United States Patent [19]

Kawai et al.

[11] Patent Number: 5,792,882
[45] Date of Patent: Aug. 11, 1998

[54] PHENOXYPHENYL CYCLOPENTENYL HYDROXYUREAS

[75] Inventors: Akiyoshi Kawai; Rodney W. Stevens, both of Handa, Japan

[73] Assignee: Pfizer Inc., New York, N.Y.

[21] Appl. No.: 591,634

[22] PCT Filed: Aug. 15, 1994

[86] PCT No.: PCT/JP94/01349

§ 371 Date: May 24, 1996

§ 102(e) Date: May 24, 1996

[87] PCT Pub. No.: WO95/05360

PCT Pub. Date: Feb. 23, 1995

[30] Foreign Application Priority Data

Aug. 19, 1993 [JP] Japan .................. 5-205453

[51] Int. Cl.⁶ .................. C07C 53/02
[52] U.S. Cl. .................. 562/623; 562/621
[58] Field of Search .................. 514/588, 595, 514/825, 826; 562/621, 623

[56] References Cited

FOREIGN PATENT DOCUMENTS

| | | |
|---|---|---|
| 384494 | 8/1990 | European Pat. Off. |
| 436199 | 7/1991 | European Pat. Off. |
| 384594 | 10/1993 | European Pat. Off. |
| WO 92/09566 | 6/1992 | WIPO |
| WO 92/09567 | 6/1992 | WIPO |
| WO 92/10469 | 6/1992 | WIPO |
| WO 93/12077 | 6/1993 | WIPO |
| WO 93/21149 | 10/1993 | WIPO |

*Primary Examiner*—Kimberly Jordan
*Assistant Examiner*—Dwayne C. Jones
*Attorney, Agent, or Firm*—Peter C. Richardson; Paul H. Ginsburg; Bryan C. Zielinski

[57] ABSTRACT

The invention relates to compounds of the formula

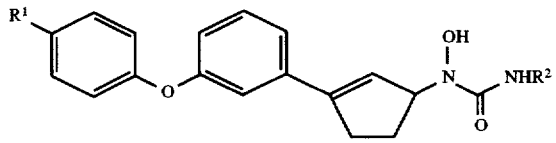

and to pharmaceutically acceptable salts thereof, wherein $R^1$ is hydrogen, fluoro, or chloro, and $R^2$ is hydrogen or methyl. The above compounds are lipoxygenase inhibitors. The invention also relates to pharmaceutical compositions containing the above compounds, and to methods of treating inflammatory and allergic conditions by administering the above compounds.

7 Claims, No Drawings

PHENOXYPHENYL CYCLOPENTENYL HYDROXYUREAS

This is a national stage application, filed pursuant to 35 U.S.C. §371, of PCT international application number PCT/JP94/01349, filed Aug. 15, 1994.

TECHNICAL FIELD

This invention relates to novel N-hydroxyurea compounds. The compounds of the present invention inhibit the action of lipoxygenase enzyme and are useful in the prevention, treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of endogenous metabolites, prostaglandins including prostacyclins, thromboxanes and leukotrienes. The first step of the arachidonic acid metabolism is the release of arachidonic acid and related unsaturated fatty acids from membrane phospholipids, via the action of phospholipase A2. Free fatty acids are then metabolized either by cyclooxygenase to produce the prostaglandins and thromboxanes or by lipoxygenase to generate hydroperoxy fatty acids which may be further metabolized to the leukotrienes. Leukotrienes have been implicated in the pathophysiology of inflammatory diseases, including rheumatoid arthritis, gout, asthma, ischemia reperfusion injury, psoriasis and inflammatory bowel diseases. Any drug that inhibits lipoxygenase is expected to provide significant new therapy for both acute and chronic inflammatory conditions.

Recently several review articles on lipoxygenase inhibitors have been reported. (See H. Masamune and L. S. Melvin, Sr., *Annual Reports in Medicinal Chemistry*, 24 (1989) pp71–80 (Academic Press) and B. J. Fitzsimmons and J. Rokach, *Leukotrienes and Lipoxygenases*, (1989) pp427–502 (Elsevier)).

More particularly, International Patent Publications Nos. WO 92/09567 and WO 92/09566 disclose a wide variety of N-hydroxyurea and hydroxamic acid compounds as inhibitors of the lipoxygenase enzyme. These include compounds of the following structural type I:

$$\text{Ar} - \text{X} - \text{A} - \underset{\underset{\text{OH}}{|}}{\text{N}} - \underset{\underset{\text{O}}{||}}{\text{C}} - \text{R} \quad \text{I}$$

in which Ar represents an aromatic group, X represents a non-aromatic ring system, A represents an optional hydrocarbon spacer group and R is either alkyl or an optionally-substituted amino group. In WO 92/09567, the non-aromatic moiety X is a saturated, carbocyclic ring having from 3 to 8 carbons, and there is no mention of the possibility of unsaturation in the X group. In WO 92/09566, the non-aromatic moiety X is shown as a carbocyclic ring having from 3 to 8 carbons, which can optionally contain a double bond. However, all of the examples of cycloalkene compounds in WO 92/09566 are cyclobutene or cyclohexene compounds and there is no suggestion that these unsaturated compounds are preferred.

Surprisingly, therefore, the present inventors have discovered that a small genus of N-hydroxyurea compounds of the general structure I, in which X is a cyclopentenyl group and Ar is an optionally-substituted 3-phenoxyphenyl group, have advantageous properties as lipoxygenase inhibitors.

BRIEF DISCLOSURE OF THE INVENTION

The present invention provides the dextrorotatory isomers of N-hydroxyurea compounds of the following chemical formula II:

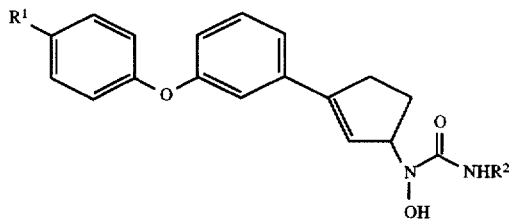

and the pharmaceutically acceptable salts thereof, wherein $R^1$ is hydrogen, fluoro or chloro; and $R^2$ is hydrogen or methyl.

The compounds of formula II inhibit the 5-lipoxygenase enzyme. Therefore they are useful for treating a medical condition for which a 5-lipoxygenase inhibitor is needed, in a mammalian subject, e.g., a human subject. The (+)-isomers are especially useful for treating or preventing allergic and inflammatory conditions. This invention also embraces pharmaceutical compositions which comprise a (+)-isomer of the formula II or a pharmaceutically acceptable salt thereof, and a pharmaceutically acceptable carrier. The (+)-isomers of the compounds of formula II show outstanding potency as lipoxygenase inhibitors. Moreover, they exhibit excellent metabolic stability towards glucuronidation.

Particularly preferred compounds of the invention are: (+)-N-[3-[3-(4-fluorophenoxy)phenyl]-2-cyclopenten-1-yl]-N-hydroxyurea; (+)-N-[3-(3-phenoxyphenyl)-2-cyclopenten-1-yl]-N-hydroxyurea; and (+)-N-[3-[3-(4-chlorophenoxy)phenyl]-2-cyclopenten-1-yl]-N-hydroxyurea.

DETAILED DESCRIPTION OF THE INVENTION

The term dextrorotatory isomer (or (+)-isomer) means the enantiomer which in ethanol solution rotates the plane of plane polarized light in a clockwise direction at the D line of sodium.

The compounds of formula II may be prepared by a number of synthetic methods. $R^1$ and $R^2$ are as previously defined.

In one embodiment, compounds of the formula 1 are prepared according to the reaction step outlined in Scheme 1:

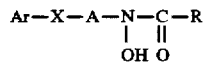

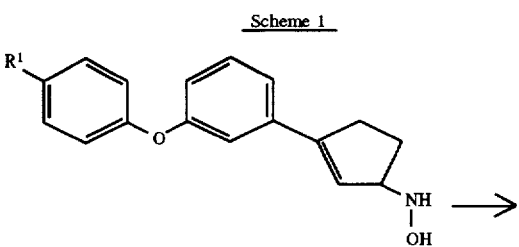

-continued
Scheme 1

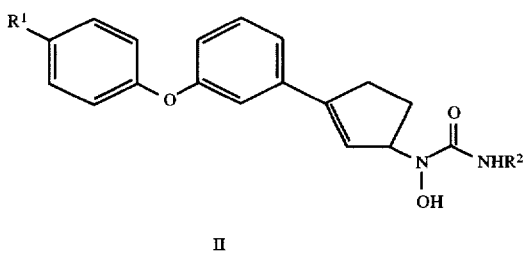

III

In this step the hydroxylamine III is treated with a suitable trialkylsilyl isocyanate or methyl isocyanate in a reaction-inert solvent usually at a temperature in the range from ambient to reflux temperature. Suitable solvents which do not react with reactants and/or products are, for example, tetrahydrofuran, dioxane, methylene chloride or benzene. An alternative procedure employs treatment of III with gaseous hydrogen chloride in a reaction-inert solvent such as benzene or toluene and then subsequent treatment with phosgene. Reaction temperatures are usually in the range from ambient temperature through to boiling point of solvent. The intermediate carbamoyl chloride is not isolated but subjected to in situ reaction with aqueous ammonia or methylamine. As a modification of this procedure, when $R^2$ is hydrogen, the acid addition salt of III may be reacted with an equimolar amount of an alkali metal cyanate, such as potassium cyanate, in water. The product of formula II thus obtained is isolated by standard methods and purification can be achieved by conventional means, such as recrystallization and chromatography.

The aforementioned hydroxylamine III may be prepared by standard synthetic procedures from the corresponding 3-substituted 2-cyclopenten-1-one or 3-substituted 2-cyclopenten-1-ol compound. For example, suitable carbonyl compound is converted to its oxime and then reduced to the requisite hydroxylamine III with a suitable reducing agent (for example, see R. F. Borch et al, J. Am. Chem. Soc., 93, 2897, 1971). Reducing agents of choice are, but not limited to, sodium cyanoborohydride and borane complexes such as borane-pyridine, borane-triethylamine and borane-dimethylsulfide. Triethylsilane in trifluoroacetic acid may also be employed.

The suitable 2-cyclopenten-1-ones can be prepared by a number of different methods (see WO 92/09566). The cyclopentenones may be prepared by the intramolecular aldol cyclization of 1,4-diketones, readily accessible from the corresponding aldehydes and methyl vinyl ketone by the Stetter reaction (for example, see L. Novak et al., Liebigs Ann. Chem., 509, 1986). Alternatively, the 2-cyclopenten-1-ones can be prepared by the cross coupling reaction of the corresponding aryl halides or triflate with the 3-stannyl-2-cyclopenten-1-one or vice versa in the presence of suitable catalyst such as $Pd(PPh_3)_4$, $PdCl_2(PPh_3)_2$ or the like (for example, see J. S. Kiely et al, J. Heterocyclic Chem., 28, 1581, 1991).

Alternatively, the aforementioned hydroxylamine III can easily be prepared by treating the corresponding 2-cyclopenten-1-ol with N,O-bis(tert-butyloxycarbonyl)-hydroxylamine under Mitsunobu-type reaction conditions followed by acid catalyzed hydrolysis (for example, employing trifluoroacetic acid) of the N,O-protected intermediate product (see Japanese Patent No. 1,045,344.). The requisite 2-cyclopenten-1-ol is readily prepared by 1,2-reduction of the corresponding 2-cyclopenten-1-one using a suitable reducing agent such as sodium borohydride, sodium borohydride-cerium trichloride or the like. The requisite alcohol may also be prepared, for example, by coupling of the corresponding aryl halide or triflate with 2-cyclopenten-1-ol in the presence of suitable catalyst such as $Pd(PPh_3)_4$ or the like.

The hydroxylamine of formula III thus obtained by the abovementioned representative procedures is isolated by standard methods and purification can be achieved by conventional means, such as recrystallization and chromatography.

In another embodiment, compounds of the formula II are prepared as illustrated in Scheme 2.

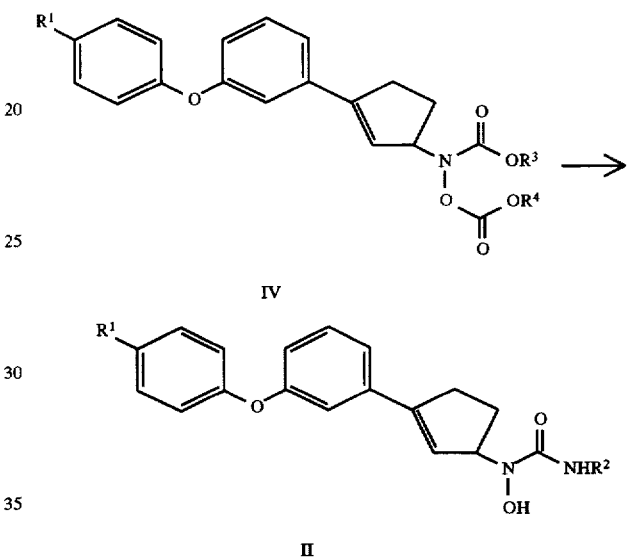

$R^3$ is phenyl, and $R^4$ is phenyl or lower alkyl.

In this process, a compound of formula IV is prepared from the corresponding cyclopentenol and bis-carboxyhydroxylamine compound, preferably N,O-bis (phenoxycarbonyl)hydroxylamine, and subsequently converted to II by treatment with ammonia, ammonium hydroxide or methylamine (A. O. Stewart and D. W. Brooks., J. Org. Chem., 57, 5020, 1992). Suitable reaction solvents are, for example, methanol, ethanol, tetrahydrofuran, benzene and the like, though reaction may be run in the absence of co-solvent, that is, in requisite amine alone. Reaction temperatures are typically in the range of ambient temperature through to boiling point of solvent. Alternatively, a compound of formula IV is prepared by direct coupling of the corresponding aryl halide or triflate with bis-carboxyhydroxylamine derived from 2-cyclopenten-1-ol in the presence of suitable catalyst such as $Pd(PPh_3)_4$ or the like. The product of formula II thus obtained is isolated by standard methods and purification can be achieved by conventional means, such as recrystallization and chromatography.

The individual dextrorotatory isomers of the compounds of the formula II may be obtained by a number of methods known to those skilled in the art. For instance, (+)-isomer of formula II may conveniently be obtained by separation of the components of the racemic mixture of formula II by means of (1) a chiral chromatography column or (2) reaction with a chiral esterifying agent, followed by separation of the diastereomeric mixture thus obtained (e.g., by chromatography), followed by regeneration of the N-hydroxyurea.

Alternatively, a chiral compound of formula II may be directly prepared from the corresponding chiral compound of formula III by methods herein previously described. The chiral compounds of formula III are readily accessible, for example, from the appropriate chiral 2-cyclopenten-1-ol. The chiral 2-cyclopenten-1-ol may conveniently be prepared by a number of methods known to those skilled in the art, including, for instance, by separation of the components of the racemic mixture by means of a chiral chromatography column or by preparing and separating suitable diastereomers and regenerating requisite resolved enantiomer, or by asymmetric synthesis.

The chiral compounds of formula II thus obtained may be purified by conventional means, such as recrystallization or the like.

The pharmaceutically acceptable salts of the novel compounds of the formula II are readily prepared by contacting said compounds with a stoichiometric amount of an appropriate metal hydroxide or alkoxide or amine in either aqueous solution or a suitable organic solvent. The respective salts may then be obtained by precipitation followed by filtration, or by evaporation of the solvent.

The compounds of formula II inhibit the activity of lipoxygenase enzyme. The ability of the compounds of the formula II to inhibit lipoxygenase enzyme makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor; e.g., allergic bronchial asthma, skin disorders, rheumatoid arthritis, osteoarthritis and thrombosis. Thus, the compounds of the formula II and their pharmaceutically acceptable salts are of particular use in the treatment or alleviation of inflammatory diseases in a human subject.

The ability of the compounds of the formula II to inhibit the activity of the lipoxygenase enzyme may be demonstrated in vitro and in vivo by the following standard procedures.

1) In vitro assay using heparinized human whole blood (HWB)

Inhibition has been demonstrated in vitro using heparinised human whole blood (*British Journal of Pharmacology*: (1990) 99, 113–118), which determines the inhibitory effect of said compounds on 5-lipoxygenase (LO) metabolism of arachidonic acid. Aliquots of heparinized human whole blood (1 ml) from healthy donors were preincubated with drugs dissolved in dimethyl sulfoxide (final concentration, 0.1%) for 10 min at 37° C., then calcium ionophore A21387 (60 µM) and Heparapid (2.5%, Sekisui Chemical Co. LTD., Japan) were added and incubations were continued for further 30 min. Reactions were terminated by rapid cooling in an ice bath. Blood-clots induced by Heparapid were removed by centrifugation. Acetonitrile (ACN, 1.5 ml) and $PGB_2$ (200 ng, as internal standard) were added to supernatants. Samples were mixed by Voltex mixer and precipitated proteins were removed by centrifugation. Supernatants were diluted to 15% ACN with water and were loaded onto prewashed Sep-Pak $C_{18}$ cartridge (Waters Associates, Milford, Miss., USA) and arachidonate metabolites were eluted with 4 ml of 70% methanol. Methanolic extract was evaporated and the residue was then reconstituted in 250 µl of 67% ACN.

ACN reconstituents (100 µl) were injected onto a reversed phase $C_{18}$ column (Wakosil SC18, 4.6×150 mm, Wako Pure Chemical Industries LTD, Japan). Column temperature was 40° C. HPLC analysis was performed by Hewlett Packard model 1090M HPLC system. The chromatographic was achieved by gradient elution using two different mobile phase ( mobile phase A consisted of 10% ACN, 0.1% trifluoroacetic acid and 0.05% triethylamine; mobile phase B consisted of 80% ACN, 0.1% trifluoroacetic acid and 0.05% triethylamine). Each mobile phase was continuously sparged with helium. The HPLC gradient was programmed as follows (where A+B=100): from 0 to 9.7 min, a linear gradient from 35 to 100% of mobile phase A with flow rate of 1 ml/min. Peaks of eluting products were quantitated by UV absorbance ($LTB_4$ and $PGB_2$ at 275 nm; HHT and 5-HETE at 235 nm, respectively) and were corrected by $PGB_2$ recovery. Linear regression was used to estimate $IC_{50}$ values.

The (+)-isomers of formula II shown in the Examples 1, 2 and 3 herein were tested in the aforementioned assay to show their ability to inhibit lipoxygenase activity. The (+)-isomers of Examples 1, 2 and 3 showed $IC_{50}$ values of around 0.5 µM.

The ability of the compounds of formula II to inhibit lipoxygenase can also be demonstrated by an assay using rat peritoneal cavity resident cells, according to the methods described in *Japanese J. Inflammation*, 7:145–150 (1987), "Synthesis of leukotrienes by peritoneal macrophages", which determines the effect of said compounds on the metabolism of arachidonic acid.

2) In vivo system measuring effects of test compound administered orally against platelet activating factor (PAF) induced lethality in mice The in vivo potency after oral administration of test compounds to ICR mice (male) was determined using the PAF lethality assay in a similar manner as that described in the following articles: J. M. Young, P. J. Maloney, S. N. Jubb, and J. S. Clark. *Prostaglandins*, 30, 545 (1985); M. Criscuoli and A. Subissi, *Br. J. Pharmac.*, 90, 203 (1987); and H. Tsunoda, S. Abe, Y. Sakuma, S. Katayama and K. Katayama, *Prostaglandins Leukotrienes and Essential Fatty Acids*, 39, 291 (1990). PAF was dissolved at a concentration of 1.2 µg/ml in 0.05 mg/ml propranolol-saline containing 0.25% bovine serum albumin (BSA) and injected intravenously into mice at a dose of 12 µg/Kg. Mortality was determined 1 hr after PAF injection. To investigate the effect of 5-LO inhibitors, compounds were dissolved in 5% tween 80, 5% EtOH-saline and administered orally (0.1 ml/10 g) 45 min prior to PAF injection. Linear regression was used to estimate $ED_{50}$ values. In this assay, the (+)-isomers of formula II of Examples 1, 2 and 3 showed $ED_{50}$ values of around 1 to 10 mg/kg.

3) In vitro glucuronidation rate studies employing monkey liver microsome preparations The major metabolic fate of hydroxyureas of structual type I is believed to be glucuronidation (D. J. Sweeny, J. Bonska, J. Machinist, R. Bell, G. Carter, S. Cepa, and H. N. Nellans, *Drug metabolism and Disposition*, 20, 328 (1992)). Compounds eliciting relative stability toward glucuronidation are thus expected to demonstrate improved in vivo pharmacokinetic properties. The stability of compounds of the present invention toward glucuronidation was assessed in vitro as described as follows.

Livers obtained from male cynomolgus monkeys (3–4 Kg) were stored at −80° C. and used within 6 months of being acquired. Livers were homogenized in 0.25M sucrose, 1 mM EDTA, 10 mM Tris (pH7.4) and microsomes prepared by standard centrifugation procedures (K. W. Bock., B. Burcbell, G. Dutton, O. Hanninen, G. J. Mulder, L. Owens, G. Siest and T. Tephly, *Biochem. Pharmacol.*, 32, 953 (1983)). Incubations were performed in 13×100 mm polypropylene tubes at 37° C. in a metabolic shaking bath (TAITEC$^R$). The final incubation volume was 2.6 ml and contained: test compound (10 µM, 30 µM, 100 µM), 2.6 mg microsomal protein, 5 mM MgCl$_2$, 0.025% Triton X-100, 50 mM Tris-HCl (pH 8.0) and 3 mM UDP-glucuronic acid. Reactions were initiated by addition of UDP-glucuronic acid and terminated by adding 200 µl of incubation mixture to 2 ml ISTD (1 µM)/acetonitrile. The precipitate was removed by centrifugation, and the supernatant was decanted and dried by Speed Vac. The residue was dissolved in 75 µl of acetonitrile/water/ammonium acetate (25:75:0.05)prior to HPLC analysis. HPLC separations were performed using a reversed phase C$_{18}$ column (WAKOSIL 5C18 φ2 mm×150 mm; 5 µm, Wako Pure Chemical Industries LTD, Japan) and chromatograph was achieved by gradient elution using two different mobile phases: mobile phase A consisted of 10% acetonitrile in 0.006N ammonium acetate; mobile phase B consisted of 80% acetonitrile in 0.006N ammonium acetate. Flow rate was 0.35 ml/min, and effluent was monitored at 260–270 nm. Microsomal protein was analyzed quantitatively by Bio-Rad protein assay using BSA as standard. The kinetics of test compound's glucuronidation were determined using a range of concentrations from 10–100 µM. Test compound's glucuronidation in monkey microsomes followed Michaelis-Menten kinetics. V$_{max}$ and K$_m$ for test compounds were estimated using Michaelis-Menten equation.

The (+)-isomers and (−)-isomers of the compounds of formula II, and mixtures thereof, exhibit excellent biological activity in vitro and in vivo against the lipoxygenase enzyme. However, in vitro glucuronidation experiments employing monkey liver microsome preparations demonstrated that the (+)-isomer is significantly more stable toward glucuronidation than the (−)-isomer. Furthermore; the (+)-isomers of formula II are more stable toward glucuronidation than structurally-related phenoxyphenylcyclopentyl hydroxyureas disclosed in WO 92/09566 and WO 92/09567. Yet further, the (+)-isomers have potency advantages as LO inhibitors over the simple phenylcyclobutenyl and phenylcyclohexenyl compounds of WO 92/09566. Also, the (+)-isomers exhibit excellent chemical stability, making them especially suitable for use in human medicine.

For treatment of the various conditions described above, the compounds and their pharmaceutically acceptable salts of formula II of this invention can be administered to a human subject either alone, or preferably in combination with pharmaceutically acceptable carriers or diluents in a pharmaceutical composition according to standard pharmaceutical practice. The compounds can be administered by various conventional routes of administration including oral, parenteral and by inhalation. When the compound are administered orally, to treat an inflammatory condition in a human subject, the dose range will be from about 0.1 to 10 mg/kg of body weight of the subject to be treated per day, preferably from about 0.5 to 10 mg/kg of body weight per day, in single or divided doses. If parenteral administration is desired, then an effective dose will be from about 0.1 to 1.0 mg/kg of body weight of the human subject to be treated per day. In some instances it may be necessary to use dosages outside these limits, since the dosages will necessarily vary according to the age and response of the individual patient as well as the type and severity of the patient's symptoms and the potency of the particular compound being administered.

For oral administration, the compounds of the invention and their pharmaceutically acceptable salts can be administered, for example, in the form of tablets, powders, lozenges, syrups, capsules, aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifing and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples. Proton nuclear magnetic resonance (NMR) spectra were measured at 270 MHz unless otherwise indicated and peak positions are expressed in parts per million (ppm) downfield from tetramethylsilane. The peak shapes are denoted as follows: s—singlet, d—doublet, t—triplet, m—multiplet and br—broad.

EXAMPLE 1

(+)-N-[3-[3-(4-Fluorophenoxy)phenyl]-2-cyclopenten-1-yl]-N-hydroxyurea

[A] 1-Bromo-3-(4-fluorophenoxy)benzene:

Solution of potassium hydroxide (32 g; 0.485M) in water (65 ml) was added dropwise to a stirred solution of 4-fluorophenol (54.42 g; 0.486M) in methanol (160 ml). After completion of addition, the mixture was evaporated and the residual solid was pulverized and taken up in N-methyl-2-pyrrolidone (200 ml). m-Bromofluorobenzene (84.97 g; 0.4855M) was added and the mixture was heated at reflux temperature overnight. After cooling, the mixture was poured into water (500 ml), extracted with Et$_2$O (500 ml×1, 200 ml×1), and the combined organic layers were washed with 2M aqueous NaOH solution (200 ml×2), water (100 ml×1), 10% aqueous HCl solution (200 ml×11), water (100 ml×1), brine (100 ml×1), dried over MgSO$_4$, and concentrated in vacuo to provide 50 g of crude ether. Distillation of the crude oil obtained (b.p. 95°–115° C.) provided 38.53 g (yield 30%) of the subtitle compound [A] as a pale yellow oil.

$^1$H-NMR (CDCl$_3$) δ; 7.24–7.14 (m, 2H), 7.10–6.96 (m, 5H), 6.89 (d, t, J=2.2 Hz, 6.9 Hz, 1H) ppm.

[B] 3-(4Fluorophenoxy)benzaldehyde:

To a cooled (−75° C.), stirred solution of 1-bromo-3-(4-fluorophenoxy)benzene (38.5 g; 0.1442M) in dry THF (80 ml) was added n-butyllithium (1.63M in n-hexane, 68 ml; 0.11M) dropwise at under N$_2$. After stirring for 30 min at −73° C., DMF (11.38 g; 0.1557M) was added dropwise to the mixture at −73° C. The mixture was stirred for further 30 min, and then allowed to warm to room temperature. 2M aqueous HCl (200 ml) was added to the mixture and the whole was extracted with Et$_2$O (100 ml×3). The combined organic layers were washed with water (150 ml), brine (150 ml), dried over MgSO$_4$, and concentrated in vacuo. The residual oil was purified by flash column (SiO$_2$) eluting with ethyl acetate-n-hexane (1: 10) to give 21.6 g of the subtitle compound [B] as a colorless oil.

¹H-NMR (CDCl₃) δ; 9.96 (s, 1H), 7.59 (d,t, J=1.1 Hz, 7.3 Hz, 1H), 7.50 (t, J=7.7 Hz, 1H), 7.42–7.40 (m, 1H), 7.28–7.23 (m, 1H), 7.11–6.99 (m, 4H) ppm.

[C] 1-[3-(4-Fluorophenoxy)phenyl]-1,4-pentanedione:

To a stirred solution of 3-(4-fluorophenoxy)benzaldehyde (26.8 g; 0.124M) in ethanol (60 ml) was added methyl vinyl ketone (8.32 ml; 0.1M), 3-benzyl-5-(2-hydroxyethyl)-4-methylthizolium chloride (5.93 g; 0.022M), and triethylamine (27.88 ml; 0.2M) at room temperature. After stirring for 6 hrs, volatiles were removed. To the residue was added water (200 ml), and the whole was extracted with ethyl acetate (150 ml×2). The combined organic layers were washed with water (100 ml), brine (100 ml), dried over MgSO₄, and concentrated in vacuo. The residual oil was purified by flash column (SiO₂) eluting with ethyl acetate-n-hexane (1:5) to give 19.03 g (yield 66.5%) of the subtitle compound [C] as a pale yellow oil.

¹H-NMR (CDCl₃) δ; 7.70 (d,t, J=1.4 Hz, 7.7 Hz, 1H), 7.54 (d,d, J=1.4 Hz, 2.2 Hz, 1H), 7.42 (t, J=8.0 Hz, 1H), 7.17 (d,d,d, J=1.1 Hz, 2.5 Hz, 8.0 Hz, 1H), 7.09–6.96 (m, 4H), 3.23 (t, J=5.9 Hz, 2H), 2.87 (t, J=5.9 Hz, 2H), 2.25 (s, 3H) ppm.

[D] 3-[3-(4Fluorophenoxy)phenyl]-2-cyclopenten-1-one:

A solution of 1-[3-(4-fluorophenoxy)phenyl]-1,4-pentanedione (19.03 g; 0.0665M) in 0.44M aqueous NaOH solution (300 ml) was refluxed for 24 hrs. After cooling, the residual solids were collected by filtration and dried to give 18 g (yield quant.) of the subtitle compound [D] as brown solids, which was used without further purification.

¹H-NMR (CDCl₃) δ; 7.41–7.38 (m, 2H), 7.26–7.23 (m, 2H), 7.10–6.97 (m, 4H), 6.53 (t, J=1.8 Hz, 1H), 3.03–2.98 (m, 2H), 2.60–2.56 (m, 2H) ppm.

[E] 3-[3-(4-Fluorophenoxy)phenyl]-2-cyclopenten-1-one oxime:

To a stirred solution of 3-[3-(4-fluorophenoxy)phenyl]-2-cyclopentenone (10 g; 0.0373M) in ethanol-pyridine (75 ml-21 ml) was added hydroxylamine hydrochloride (3.37 g; 0.0485M) at room temperature. After stirring for 4 hrs, solvent was removed. To the residue was added dilute aqueous HCl (100 ml), and the whole was extracted with ethyl acetate (200 ml×1, 100 ml×1). The combined organic layers were washed with water (100 ml), brine (100 ml), dried over MgSO₄, and concentrated in vacuo to give 12 g of crude subtitle compound [E] as a brown oil, which was used without further purification.

[F] N-[3-[3-(4-Fluorophenoxy)phenyl]-2-cyclopenten-1-yl]-N-hydroxyl-amine:

To a stirred solution of 3-[3-(4-fluorophenoxy)phenyl]-2-cyclopentenone oxime (1.85 g; 6.54 mM) in acetic acid (10 ml) was added sodium cyanoborohydride (0.62 g; 9.81 mM) portionwise at room temperature. After stirring for 2 hrs, additional sodium cyanoborohydride (0.25 g; 4 mM) and acetic acid (5 ml) was added. The mixture was stirred overnight. Acetic acid was removed in vacuo, and to the residue was added saturated aqueous NaHCO₃ (50 ml). The whole was extracted with ethyl acetate (50 ml×1, 30 ml×1), and the combined organic layers were washed with water (50 ml), brine (50 ml), dried over MgSO₄, and concentrated in vacuo. The residual oil was purified by flash column (SiO₂) eluting with CH₂Cl₂-ethanol (30:1) to give 1.07 g of the subtitle compound [F] as a pale yellow oil.

¹H-NMR (CDCl₃) δ; 7.32–7.18 (m, 2H), 7.08–6.85 (m, 6H), 6.14 (d, J=2.2 Hz, 1H), 5.90–5.30 (br.d, 2H), 4.32 (br.s, 1H), 2.90–2.81 (m, 1H), 2.73–2.62 (m, 1H), 2.37–2.23 (m, 1H), 2.06–1.93 (m, 1H) ppm.

[G] N-[3-[3-(4-Fluorophenoxy)phenyl]-2-cyclopenten-1-yl]-N-hydroxyurea:

To a stirred solution of N-[3-[3-(4-fluorophenoxy)phenyl]cyclopent-2-enyl]-N-hydroxylamine (1.07 g; 3.75 mM) in dry THF (10 ml) was added trimethylsilyl isocyanate (0.76 g; 5.63 mM) at room temperature. After stirring for 1 hr, ethanol (10 ml) was added. Volatiles were removed, and the resulting solids were recrystallized from ethyl acetate-n-hexane to give 0.6 g (y. 28%) of the subtitle compound [G] as colorless solids.

m.p. 151°–153° C. (dec.)

¹H-NMR (DMSO-d₆) δ; 8.92 (s, 1H), 7.36 (t, J=8.1 Hz, 1I), 7.28–7.20 (m, 3H), 7.11–7.04 (m, 3H), 6.89–6.85 (m, 1H), 6.32 (s, 2H), 6.08 (d, J=2.2 Hz, 1H), 5.33 (br.s, 1H), 2.79–2.69 (m, 1H), 2.59–2.48 (m, 1H), 2.18–2.06 (m, 1H), 2.00–1.88 (m, 1H) ppm.

IR (nujol) cm⁻¹; 3460, 1655, 1575, 1170, 1090, 840, 775.

Anal. Calcd. for $C_{18}H_{17}FN_2O_3$: C, 65.85, H, 5.22, N, 8.53, F, 5.79; found: C, 65.87, H, 5.26, N, 8.43, F, 5.92.

(+)-N-[3-[3-(4-Fluorophenoxy)phenyl]-2-cyclopenten-1-yl]-N-hydroxyurea:

The title dextrorotatory enantiomer was obtained by separation on a chiral stationary phase of the racemate obtained as [G]. The racemate (50 mg) was resolved by HPLC (eluant; n-hexane-ethanol (70:30)) using a chiral pak AS column (DAICEL CHEM. IND.) to give 12 mg of the less polar title enantiomer after recrystallization from ethyl acetate-n-hexane as colorless crystals.

m.p. 152°–154° C.; [α]_D=+59.6 (C=0.057, ethanol)

Example 2

(+)-N-[3-(3-Phenoxyphenyl)-2-cyclopenten-1-yl]-N-hydroxyurea

N-[3-(3-Phenoxyphenyl)-2-cyclopenten-1-yl]-N-hydroxyurea:

The subtitle compound was prepared according to the procedure of Example 1 using 3-phenoxybenzaldehyde instead of 3-(4-fluorophenoxy)benzaldehyde in step [C].

m.p. 147°–148° C. (dec.).

¹H-NMR (DMSO-d₆) δ; 8.92 (s, 1H), 7.42–7.26 (m, 4H), 7.17–7.11 (m, 2H), 7.03–6.98 (m, 2H), 6.92–6.88 (m, 1H), 6.32 (s, 2H), 6.08 (d, J=2.2 Hz, 1H), 5.33 (br.s, 1H), 2.74–2.67 (m, 1H), 2.57–2.48 (m, 1H), 2.18–2.05 (m, 1H), 1.99–1.86 (m, 1H).

IR (nujol) cm⁻¹; 3450, 1655, 1575, 1170, 770, 690.

Anal. Calcd. for $C_{18}H_{18}N_2O_3$: C, 69.66, H, 5.85, N, 9.03; found: C, 69.51, H, 5.81, N, 8.94.

(+)-N-[3-(3-Phenoxyphenyl)-2-cyclopenten-1-yl]-N-hydroxyurea:

The title dextrorotatory enantiomer was obtained by separation on a chiral stationary phase of the racemate N-[3-(3-phenoxyphenyl)-2-cyclopenten-1-yl]-N-hydroxyurea. The racemate (50 mg) was resolved by HPLC (eluant; n-hexane-ethanol (70:30)) using a chiral pak AS column (DAICEL CHEM. IND.) to give 12 mg of the less polar enantiomer after recrystallization from ethyl acetate-n-hexane as colorless crystals.

m.p. 139°–141° C.; ($[\alpha]_D$=+61.7 (C=0.06, ethanol)

Example 3

(+)-N-|3-|3-(4-Chlorophenoxy)phenyl|-2-cyclopenten-1-yl|-N-hydroxyurea

N-|3-|3-(4-Chlorophenoxy)phenyl|-2-cyclopenten-1-yl|-N-hydroxyurea:

The subtitle compound was prepared according to the procedure of Example 1 using 3-(4-chlorophenoxy)benzaldehyde instead of 3-(4-fluorophenoxy)benzaldehyde in step |C|.

m.p. 145.5°–146.5° C. (dec.).

$^1$H-NMR (DMSO-d$_6$) δ; 8.92 (s, 1H), 7.43 (d, J=8.7 Hz, 2H), 7.39–7.29 (m, 2H), 7.15 (s, 1H), 7.03 (d, J=8.7 Hz, 2H), 6.95–6.91 (m, 1H), 6.32 (s, 2H), 6.11 (s, 1H), 5.33 (br.s. 1H), 2.80–2.68 (m, 1), 2.58–2.47 (m, 1H), 2.18–2.08 (m, 1H), 1.97–1.90 (m, 1H).

IR (nujol) cm$^{-1}$; 3470, 1622, 1563, 1510, 1490, 1230, 1185, 1090, 1010, 820.

Anal. Calcd. for $C_{18}H_{17}ClN_2O_3$: C, 62.70, H, 4.97, N, 8.12, Cl, 10.28; found: C, 62.88, H, 4.98, N, 8.19, Cl, 10.22.

(+)-N-|3-|3-(4-Chlorophenoxy)phenyl|-2-cyclopenten-1-yl|-N-hydroxyurea:

The title dextrorotatory enantiomer was obtained by separation on a chiral stationary phase of the racemate N-|3-|3-(4-chlorophenoxy)phenyl|-2-cyclopenten-1-yl|-N-hydroxyurea. The racemate (50 mg) was resolved by HPLC (eluant; n-hexane-ethanol (70:30)) using a chiral pak AS column (DAICEL CHEM. IND.) to give 12 mg of the less polar enantiomer after recrystallization from ethyl acetate-n-hexane as colorless crystals.

m.p. 143°–144° C.; $[\alpha]_D$=+61.4 (C=0.044, ethanol)

We claim:

1. The dextrorotatory isomer of a compound of the following chemical formula:

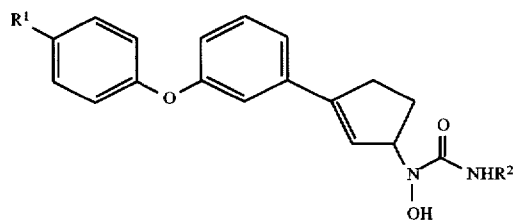

and the pharmaceutically acceptable salts thereof, wherein $R^1$ is hydrogen, fluoro or chloro; and $R^2$ is hydrogen or methyl.

2. A compound according to claim 1, wherein $R^2$ is hydrogen.

3. The dextrorotatory isomer of N-|3-|3-(4-fluorophenoxy)phenyl|-2-cyclopenten-1-yl|-N-hydroxyurea, a compound according to claim 1.

4. A pharmaceutical composition for the treatment of a medical condition for which a 5-lipoxygenase inhibitor is needed, in a mammalian subject, which comprises a therapeutically effective amount of a compound according to claim 1, and a pharmaceutically-acceptable carrier.

5. A pharmaceutical composition for the treatment of an allergic or inflammatory condition in a mammalian subject, which comprises a therapeutically effective amount of a compound of claim 1 and a pharmaceutically acceptable carrier.

6. A method for the treatment of a medical condition for which a 5-lipoxygenase inhibitor is needed, in a mammalian subject, which comprises administering to said subject a therapeutic amount of a compound according to claim 1.

7. A method according to claim 6, wherein the medical condition is an allergic or inflammatory condtion.

* * * * *